(12) United States Patent
Heiser (10) Patent No.: US 7,967,603 B2
(45) Date of Patent: Jun. 28, 2011

(54) SELF-LIGATING ORTHODONTIC BRACKET

(76) Inventor: Wolfgang Heiser, Innsbruck (AT)

( * ) Notice: Subject to any disclaimer, the term of this patent is extended or adjusted under 35 U.S.C. 154(b) by 218 days.

(21) Appl. No.: 12/343,593

(22) Filed: Dec. 24, 2008

(65) Prior Publication Data

US 2009/0170049 A1    Jul. 2, 2009

(30) Foreign Application Priority Data

Dec. 27, 2007  (DE) .......................... 10 2007 062 735

(51) Int. Cl.
*A61C 7/12*    (2006.01)
(52) U.S. Cl. .......................................... 433/10
(58) Field of Classification Search .................. 433/8, 9, 433/10, 11, 13, 14
See application file for complete search history.

(56) References Cited

U.S. PATENT DOCUMENTS

| | | | | |
|---|---|---|---|---|
| 4,634,662 A | * | 1/1987 | Rosenberg | 433/10 |
| 4,712,999 A | * | 12/1987 | Rosenberg | 433/8 |
| 5,474,445 A | * | 12/1995 | Voudouris | 433/10 |
| 5,562,444 A | | 10/1996 | Heiser et al. | |
| 5,685,711 A | | 11/1997 | Hanson | |
| 6,776,613 B2 | * | 8/2004 | Orikasa | 433/11 |
| 6,942,483 B2 | | 9/2005 | Heiser | |
| 2006/0110699 A1 | * | 5/2006 | Forster | 433/11 |
| 2007/0072143 A1 | * | 3/2007 | Sommer | 433/10 |
| 2007/0243497 A1 | | 10/2007 | Voudouris | |

FOREIGN PATENT DOCUMENTS

EP    1 452 148    9/2004

* cited by examiner

*Primary Examiner* — Ralph A Lewis
(74) *Attorney, Agent, or Firm* — Jansson Shupe & Munger Ltd.

(57) ABSTRACT

A self-ligating orthodontic bracket with a closing spring (7) made of spring steel sheet, which has a first end (22), which can be anchored to the first tie wing (4a), and a second end, which is connected to the first end (22) by an arc (21) wrapping around the first tie wing (4a) and which is formed by three tongues, at least one of which is a ligating tongue (8) and at least one a latching tongue (9). The tongues are separated from each other by notches (10) and the closing spring (7) is connected detachably to the upper bracket structure (4). The tongues are essentially parallel to each other; and in the closed position of the closing spring (7), the ligating tongue (8) is pre-tensioned in the direction toward an arch wire receiving slot (5) formed between the tie wings (4a, 4b). Latching tongue (9) is retained by at least one projection (13) formed on the bracket, such projection being provided with an undercut (12), in which the free edge of the latching tongue (9) lies when the closing spring (7) is in the closed position.

13 Claims, 9 Drawing Sheets

SELF-LIGATING ORTHODONTIC BRACKET

CROSS REFERENCE TO RELATED APPLICATION

This application claims priority based on German patent application DE 10 2007 062 735.3, filed Dec. 27, 2007.

FIELD OF THE INVENTION

The invention pertains to a self-ligating orthodontic bracket. A bracket of this type is known from U.S. Pat. No. 6,942,483 B2.

BACKGROUND

Orthodontic brackets consist basically of a base plate and an upper structure, which extends upward from the base plate and in which a slot is formed to receive an arch wire. Brackets are cemented by their base plates to the teeth of the row to be corrected, and an arch wire is inserted through the slots of all of the brackets attached to the row of teeth and secured in position there by a ligature, which is anchored to the upper structure and extends across the arch wire lying in the slot. Although only rings of elastic material, which were wrapped around tie wings formed on the upper structure, were used in the past as ligatures, so-called "self-ligating" brackets have been in use for many years, wherein the elastic rings are replaced by closing mechanisms, preferably spring elements, which are anchored on the upper structure of the bracket. Changing the arch wire, which must be done several times during the course of an orthodontic treatment, thus becomes less time-consuming.

DESCRIPTION OF THE PRIOR ART

The closing spring of a self-ligating bracket must be secured in its closed position to prevent it from opening unintentionally. The bracket according to U.S. Pat. No. 6,942,483 B2 comprises a closing spring consisting of a spring steel sheet permanently attached to the upper bracket structure. To serve the indicated purpose, this closing spring is provided with a latching tongue, which is stamped out between two parallel ligating tongues of the closing spring, which extend across the wire receiving slot. The latching tongue is bent essentially at a right angle to those tongues. The latching tongue is bent again at its free end, so that it can engage underneath a retaining projection formed on the upper bracket structure, when the spring is in the securing position, i.e. the position in which the ligating tongues extend transversely across the slot and the wire present therein.

A self-ligating orthodontic bracket is known from U.S. Pat. No. 5,685,711 A, the closing spring of which consists of a ligating arm extending across the slot and a locking arm extending over and essentially parallel to the ligating arm. The two arms are connected to each other by a connecting section, which is bent into a circle and which cooperates with pins formed on the upper bracket structure to form a hinge. The closing spring can pivot between an open position, which makes the slot freely accessible, and a closed position. During production, the upper structure of the bracket is assembled from two halves, which are essentially mirror images of each other, between which the closing spring is inserted when the two halves are being assembled. The two halves of the upper bracket structure are then welded together by means of a laser tool. It is therefore impossible to replace the closing spring if it becomes damaged.

U.S. Pat. No. 5,562,444 A discloses a bracket with a movable but captured closing spring, wherein the closing spring is formed without a fork and is held immovably and undeformably only by its intrinsic elastic force in the opened or closed position. Specifically, the force which the closing spring exerts on the arch wire is determined only by the type of material selected for the closing spring and therefore cannot be adjusted. U.S. Pat. No. 5,562,444 A also discloses projections on the second bracket tie wing, under which, in the closed position, the terminal edge of the closing spring lies, so that the spring cannot be opened unintentionally. The projections are not able to produce any pre-tension in the closing spring.

SUMMARY OF THE INVENTION

It is therefore the object of the present invention to provide an orthodontic bracket with a replaceable closing spring which can be produced by means of a simple stamping and bending process. In addition, it would be desirable to provide an orthodontic bracket which can be easily pivoted between an opened and a closed position by means of a simple tool.

In a first embodiment of the invention, the latching tongue, which holds the closing spring consisting of a spring steel sheet in its closed position on the upper structure of the bracket is stamped out between the ligating tongues. In contrast to the tongue described just above, however, the latching tongue is relatively short and is not bent out of the plane which defines the ligating tongues. On the contrary, it extends between the plane defining the latching and ligating tongues all the way to its free end essentially in the same plane as those tongues. In the closed position of the spring, the free edge area of the latching tongue fits under a projection formed on the upper bracket structure; the cooperation between the latching tongue and this projection prevents the closing spring from being opened unintentionally. If it is desired to open the closing spring, it is sufficient to simply use a needle-like tool to disengage the latching tongue from the latching projection. It is especially effective for the latching projection to be divided in the middle by a gap extending transversely to the direction in which the wire receiving slot extends, so that the free edge of the latching tongue is accessible to the needle-like tool, with the result that the latching tongue can be pushed transversely to the slot and thus disconnected from its locking engagement.

The force applied to the latching tongue by the tool between the ligating tongues makes it possible for the latching tongue to be pushed elastically out of engagement with the latching projection of the upper bracket structure.

In a second embodiment of the invention, only one ligating tongue is present being located between two latching tongues. In this second embodiment, when the closing spring is in the closed position, the tongues extend across the arch wire receiving slot. The free ends of said latching tongues engage in undercuts, which are formed on the upper bracket structure.

In both embodiments, when the closing spring is in the closed position, the ligating tongue(s) are pre-tensioned in the direction toward the arch wire slot (possibly to different degrees), so that a force can be exerted on the arch wire present in the slot, namely, a force which makes it possible to use the bracket as a so-called "active" bracket, in which the closing spring not only secures the arch wire in its slot but also can actively produce a torque towards the arch wire slot and, depending on the arch wire position, on the arch wire itself.

The spring can be anchored on the upper bracket structure in the same manner as that described in U.S. Pat. No. 5,562,444 A or in U.S. Pat. No. 6,942,483 B2. The present invention can be realized in an especially advantageous manner in combination with an attachment method in which the anchoring end of the closing spring forms part of a hinge, because, as a result, the arc between the tongues and the anchoring point becomes comparatively short. In turn the elastic restoring forces, which keep the spring in its closed position, become stronger. According to the invention, a bore extending parallel to the wire slot is formed in the bracket tie wing around which the arc of the closing spring is wrapped. The tie wing comprises a gap extending transversely to the wire receiving slot, a gap which divides the tie wing into two halves a certain distance apart and into which the arc-like section of reduced width of the closing spring extends, this section being provided on each side of its free end with a tab, each of which can be inserted into one of the bores in the bracket tie wing.

To avoid the upper bracket structure having to be produced as two separate parts to allow the mounting of the spring, as described in the case of the bracket according to U.S. Pat. No. 5,685,711 A, the bore in one of the two halves of the wing has a radially oriented feed slot. In the assembled state of the spring, this feed slot is advisably closed off by a bearing bush, which is introduced into the bore and surrounds the tab of the closing spring present there.

This way of supporting the closing spring is independent of the way in which the closing spring is secured in its closed position, but it can be applied to especially advantageous effect in the case of the inventive bracket.

How these and other objects are accomplished will become apparent from the following descriptions and the drawings.

BRIEF DESCRIPTION OF THE DRAWINGS

The invention is explained in greater detail below with reference to the exemplary embodiments shown in the drawings.

DETAILED DESCRIPTION OF THE INVENTION

FIGS. 1-9 illustrate preferred embodiments of the orthodontic bracket in accordance with this invention. Common or similar parts are given the same numbers in the drawings of all embodiments.

Figure 1:
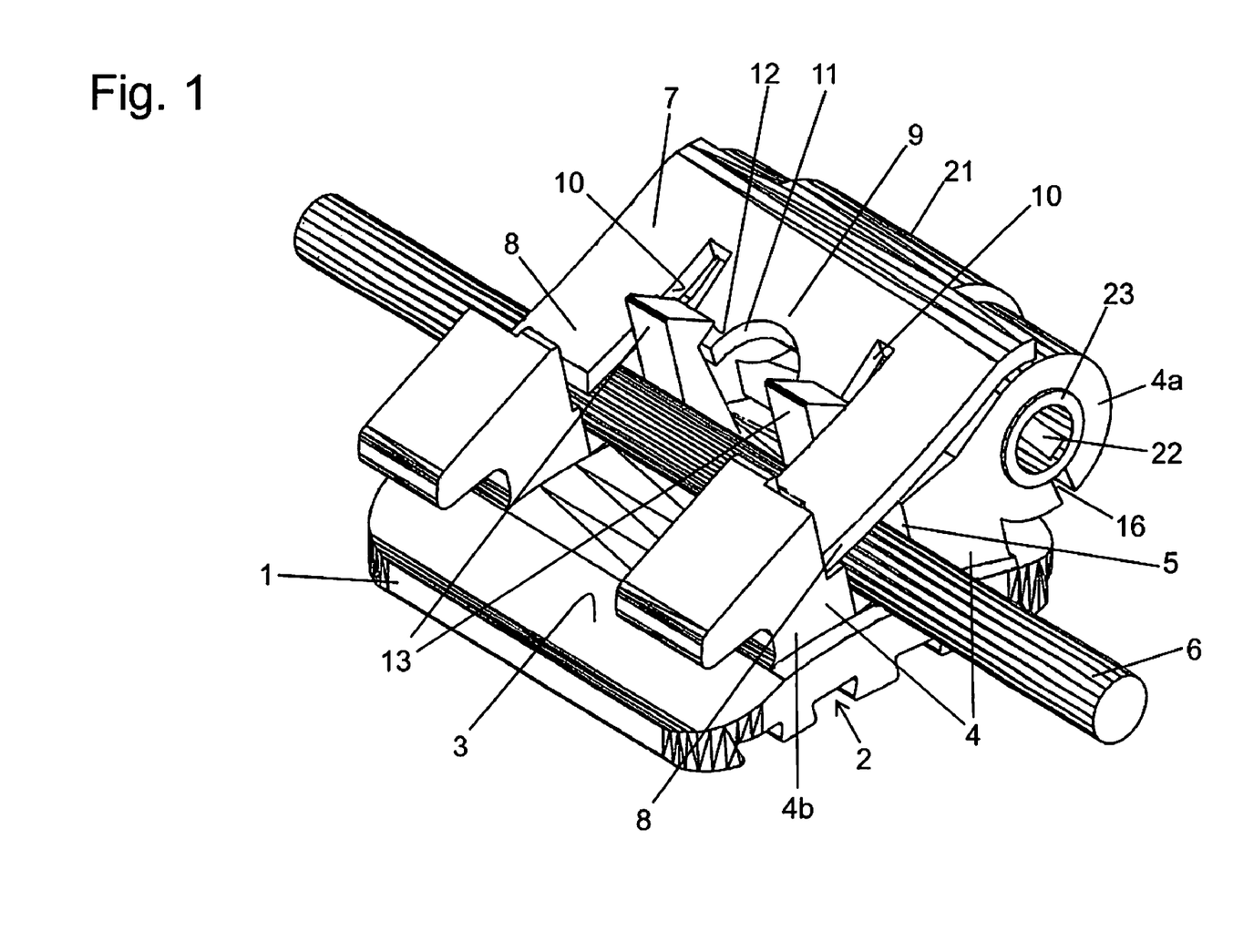
FIG. 1 shows a perspective view of a first embodiment of an inventive bracket with an arch wire inserted therein.

FIG. 1 shows a first embodiment of the self-ligating orthodontic bracket according to the invention in the closed state of its closing spring with an arch wire held in place.

The bracket according to FIG. 1 has a base plate 1 comprising a bottom side 2 for attachment to a tooth and a top side 3. An upper structure, designated overall by the number 4, extends upward from the top side. The upper structure comprises a first tie wing 4a and a second tie wing 4b. Between the two tie wings 4a and 4b, there extends a slot 5, in which an arch wire 6 is held, which is not a component of the bracket. The tie wings 4a and 4b have a gap extending transversely to the longitudinal dimension of the slot 5, a gap which divides each of the wings into two halves a predetermined distance apart.

A closing spring, designated overall by the number 7, which preferably consists of high-grade spring steel sheet, also forms part of the bracket. The closing spring 7 has a first end, which is anchored to the first tie wing 4a of the upper bracket structure 4 in a manner to be described further below. The closing spring 7 also has a second end, which is formed by three tongues, namely, two parallel ligating tongues 8, which extend transversely across the slot 5 and the arch wire 6 located therein, and a latching tongue 9, which extends between the two ligating tongues 8 and is bounded by two notches 10 in the spring steel sheet. The latching tongue 9 is of a dimension that it does not extend across the slot 5. At its free edge, i.e., the edge near the slot 5, it has an essentially semicircular recess 11 to accept a pin-like tool. In the closed position of the closing spring 7 shown, the free edge of the latching tongue 9 next to the recess 11 lies under an undercut 12, which is formed on a projection 13. This projection also has a gap extending transversely to the wire receiving slot 5, so that the recess 11 in the free edge of the latching tongue 9 is accessible to the previously mentioned pin-like tool, which can be introduced between the latching tongue 9 and the arch wire 5 and then used to push the latching tongue 9 away from the arch wire 5.

When the closing spring 7 is in the closed position, the two ligating tongues 8 are centered on the projections 13 by lateral contact.

Figure 2:
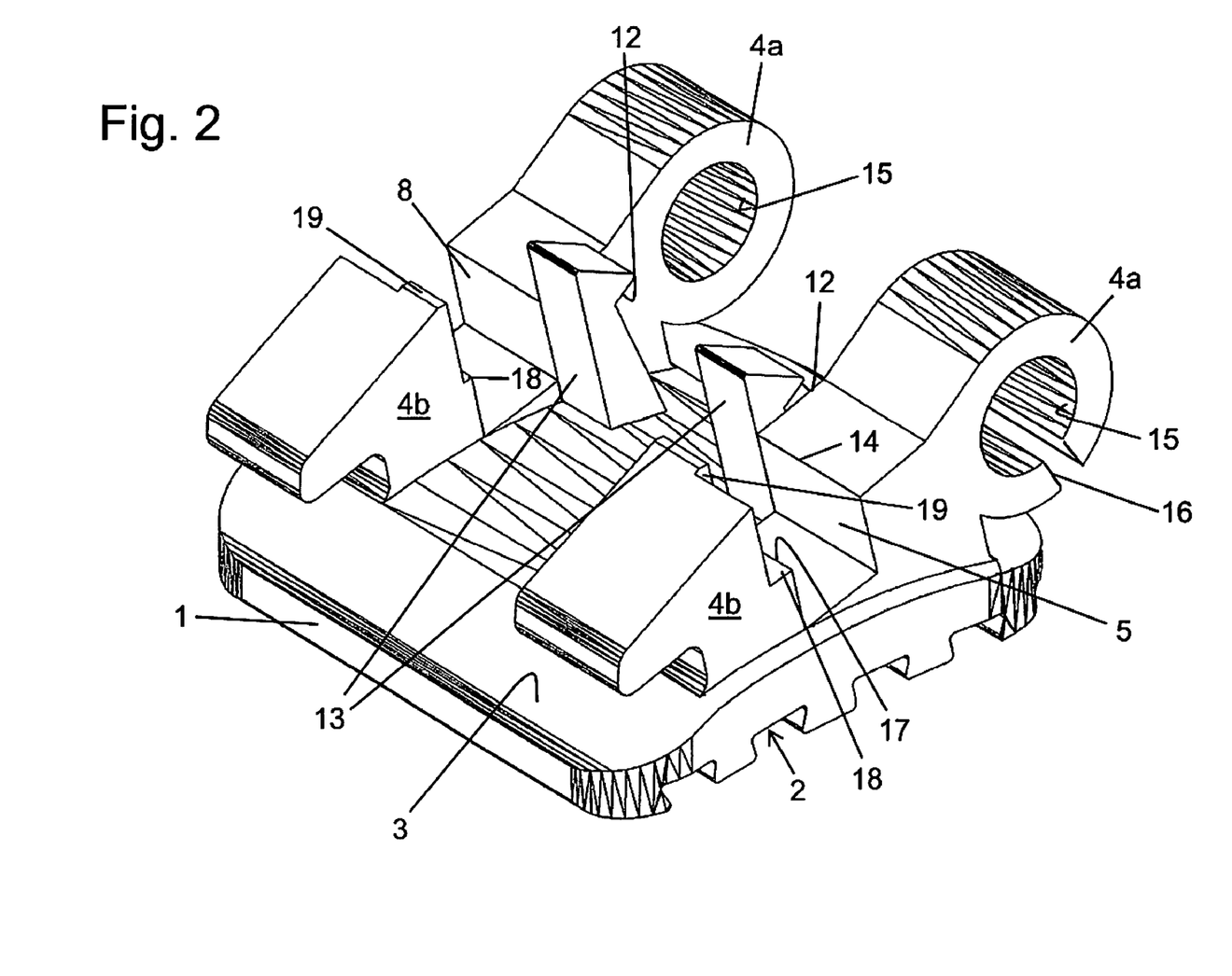
FIG. 2 shows a perspective view of the bracket of FIG. 1 without the closing spring.

As can be seen in FIG. 2, undercut 12 on the projection 13 is located at a level approximately the same as that of upper edge 14. In this embodiment, upper edge 14 forms a boundary of the wire receiving slot 5 on the side of the first tie wing 4a of upper bracket structure 4.

It can also be seen that, in the first tie wing 4a, which is divided by the gap, a bore 15 extending parallel to the longitudinal direction of the slot 5 is formed. In one of the two halves of the first tie wing 4a, the bore 15 has a radial feed slot 16 facing the top side 3 of the base plate 1. This feed slot makes it possible for the closing spring to be mounted on the finished upper bracket structure 4 in a manner to be described further below.

As can also be seen in FIG. 2, the slot 5 has, on the side of the second tie wing 4b, an upper edge 17, proceeding from which a contact surface 18 for the ligating tongues 8 extends. From the contact surface 18, a projection 19 extends upward from each of the two halves of the second tie wing 4b, which is interrupted by the gap. The projections 19 are symmetric to each other. As will be explained in detail below, projections 19 help to center the closing spring 7.

Figure 3:
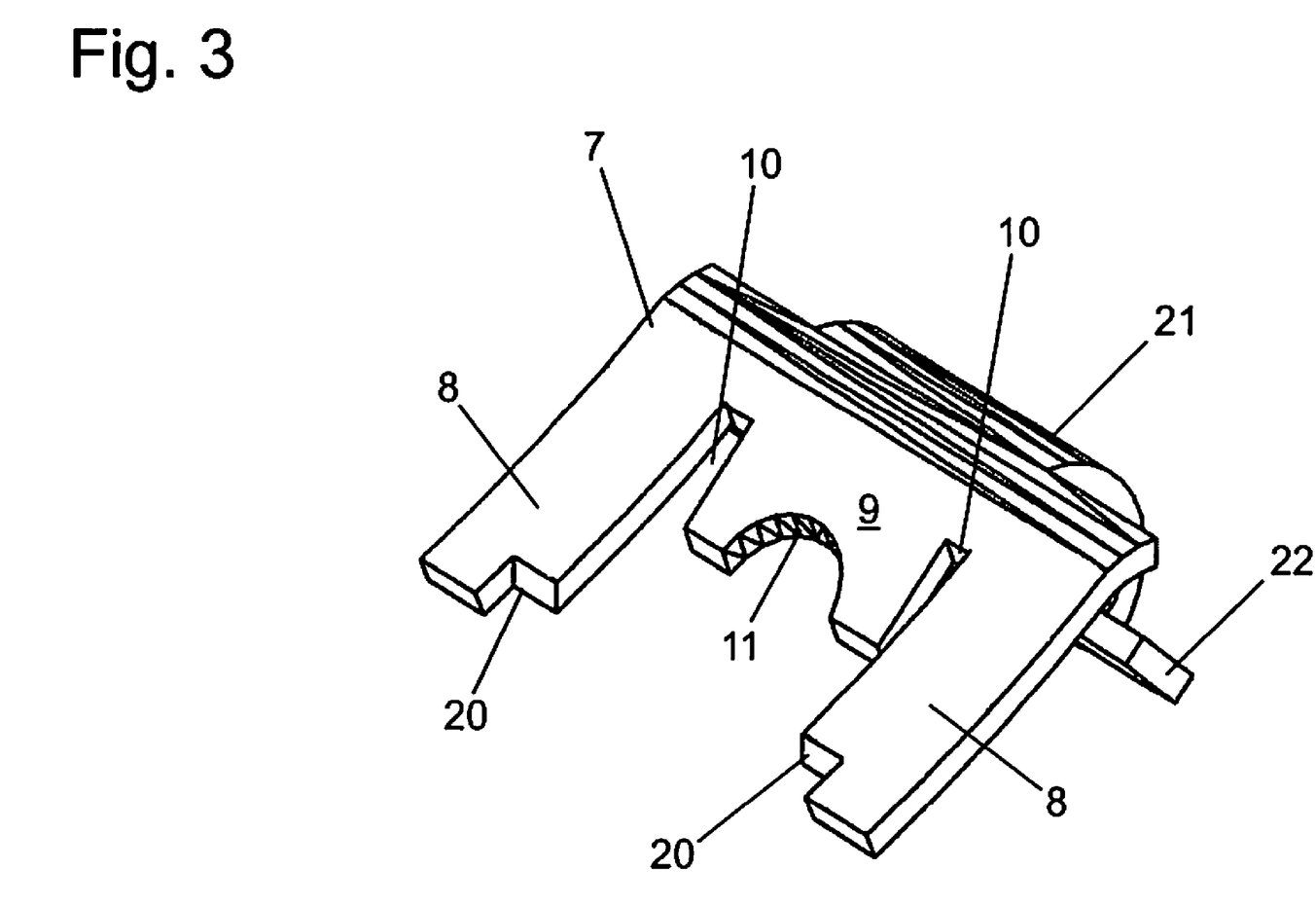
FIG. 3 shows a perspective view of the closing spring of the bracket of FIG. 1.

As shown in FIG. 3, closing spring 7 has a cutout 20 at the free end of each of the ligating tongues 8. The cutouts 20 cooperate with the projections 19 on the contact surface 18 to center the closing spring 7 and to prevent it from sliding sideways when the free ends of the ligating tongues 8 arrive in the closed position and finally rest on the contact surfaces 18 of the second tie wing 4b (see FIG. 1).

It can be seen in FIG. 3 that an arc 21, which is of reduced width, adjoins the root area where the ligating tongues 8 and the interposed latching tongue 9 of the closing spring 7 merge with each other. Such structure can be seen in FIGS. 7a and 7b. Adjoining each side of the end of the arc 21 of reduced width is a tab 22, only one of which can be seen in FIG. 3. The width of the reduced-width area is calculated in such a way that the arc-like section 21 of the closing spring can fit between the two halves, created by the gap, of the first tie wing 4a.

Figure 4:
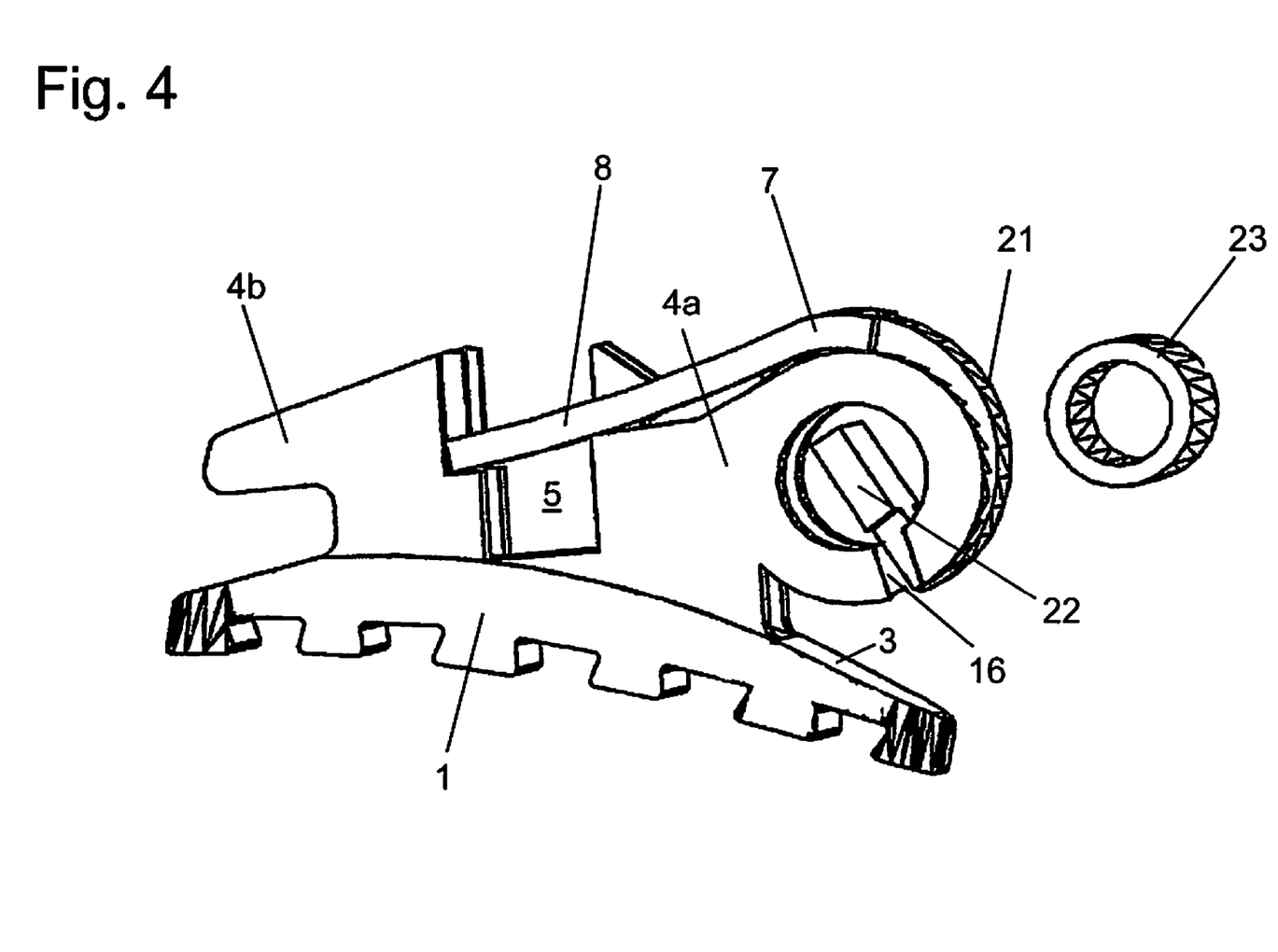
FIG. 4 shows a side view of the bracket of FIG. 1 in the closed position of the spring, without the arch wire and with a separately illustrated bearing bush.

FIG. 4 shows a side view of the bracket of FIG. 1 in an almost completed state. As can be seen, the tab 22 is held in the bore 15 in the one half of the first tie wing 4a with a certain amount of play. To prevent the tab 22 from hooking onto the edges of the feed slot 16 when the closing spring 7 is opened or closed, a bearing bush 23 is provided, which is pushed, or preferably pressed, into the bore 15 to cover the feed slot 16 after the closing spring 7 has been attached to the bracket. The final assembled state is easily recognized in FIG. 1. So that the bore 15 (FIG. 2) can have the same diameter in both halves of the first tie wing 4a, the tab 22 held by the bearing bush 23 is advisably made narrower than the other tab by the amount necessary to avoid a skewed seating of the closing spring 7. Such structure is most easily seen in FIGS. 7a and 7b.

Figure 5A:
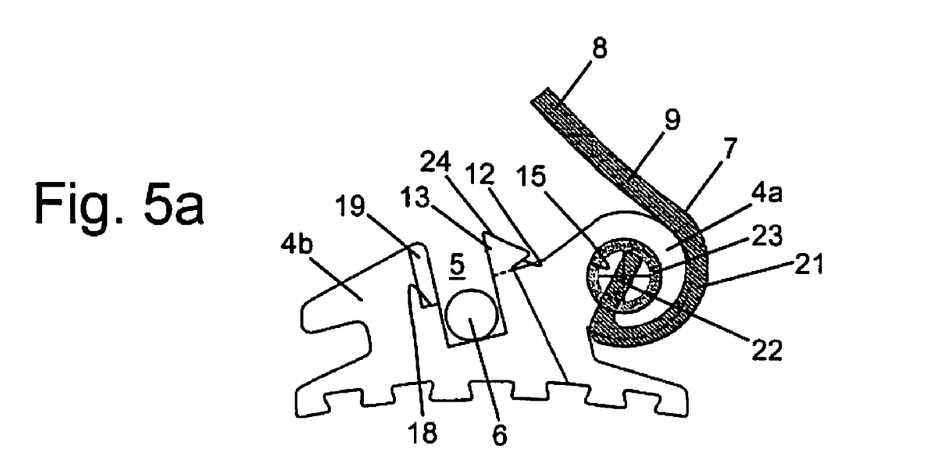
FIGS. 5a-5c show the bracket of FIG. 1 from the side with the closing spring in different positions.
Figure 5B:
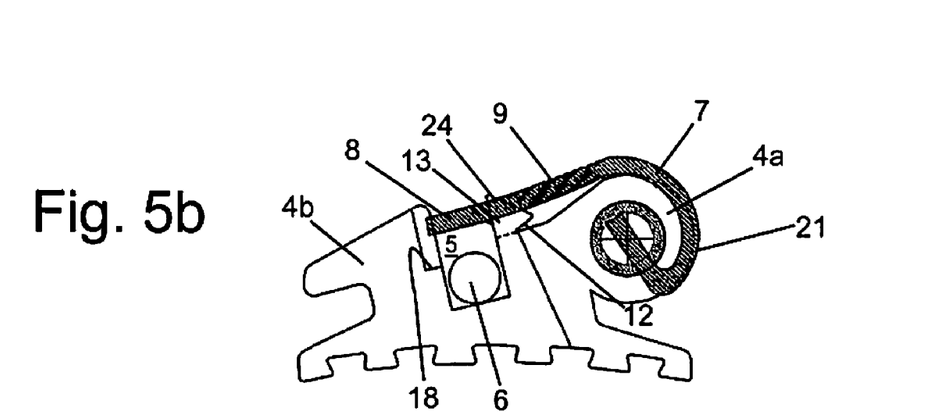

FIG. 5a shows the bracket from the side in the completely opened state of the closing spring 7. It can be seen that the closing spring 7 has been pivoted around the hinge formed by the bore 15 with the help of the tabs 22 into the opened, end position. The ligating tongues 8 and the latching tongue 9 are relaxed and extend parallel to each other; that is, they are aligned with each other on the same plane. In FIG. 5b, the closing spring 7 has been pivoted into a position in which the ligating tongues 8 extend across the slot 5 with the arch wire 6 present therein. The free edge of the latching tongue 9 rests on a slanted surface 24, which is formed on projection 13.

Figure 5C:
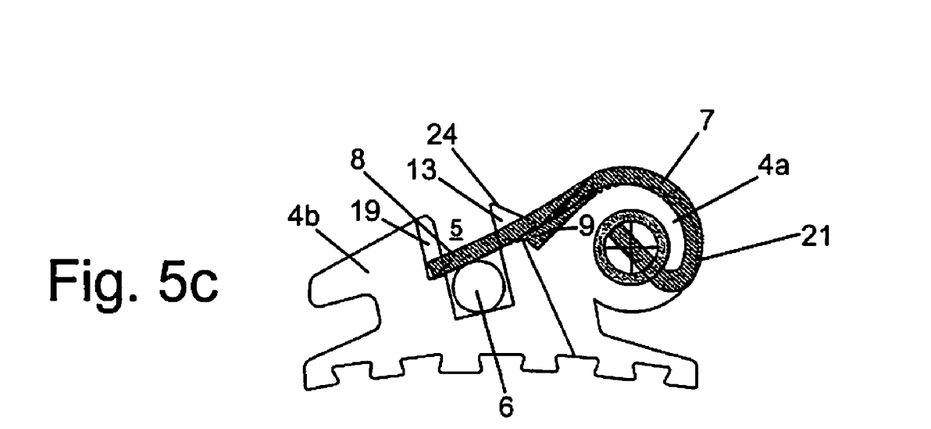

By pressing further the latching tongue 9 from above and possibly also by pressing the spring toward the right in the view according to FIG. 5b, the free edge of the latching tongue 9 moves downward over the slanted surface 24 until it slides under the undercut 12, which is formed on the projection 13. This position is shown in FIG. 5c. In this position, the closing spring 7 is secured in its closed position. So that enough force can be produced to hold the arch wire 6 in position, the undercut 12 is located at a level which is approximately the same as that of the upper edge 18 of the slot 5 in the side of the first tie wing 4a. Undercut 12 can be somewhat higher or lower, depending on whether and to what extent the latching tongue 9 is bent in the relaxed state with respect to the plane described by the ligating tongues 8. To bring the latching tongue 9 into the latching position, it must be pushed down. When latching tongue 9 in its latching position, that is, in the position in which the closing spring is closed, it produces an elastic tension in the closing spring, pressing the ligating tongues downward onto the arch wire. When the free ends of the ligating tongues 8 are resting on the contact surfaces 18 on the first tie wing (see FIG. 5c), the tongues are bent toward the arch wire 6. In order to release the closing spring 7 from this position, it is sufficient to simply push the latching tongue 9 toward the right until it is free of the undercut 12, which is made possible by the elasticity of the arch 21, which can escape to the right.

Figure 6A:
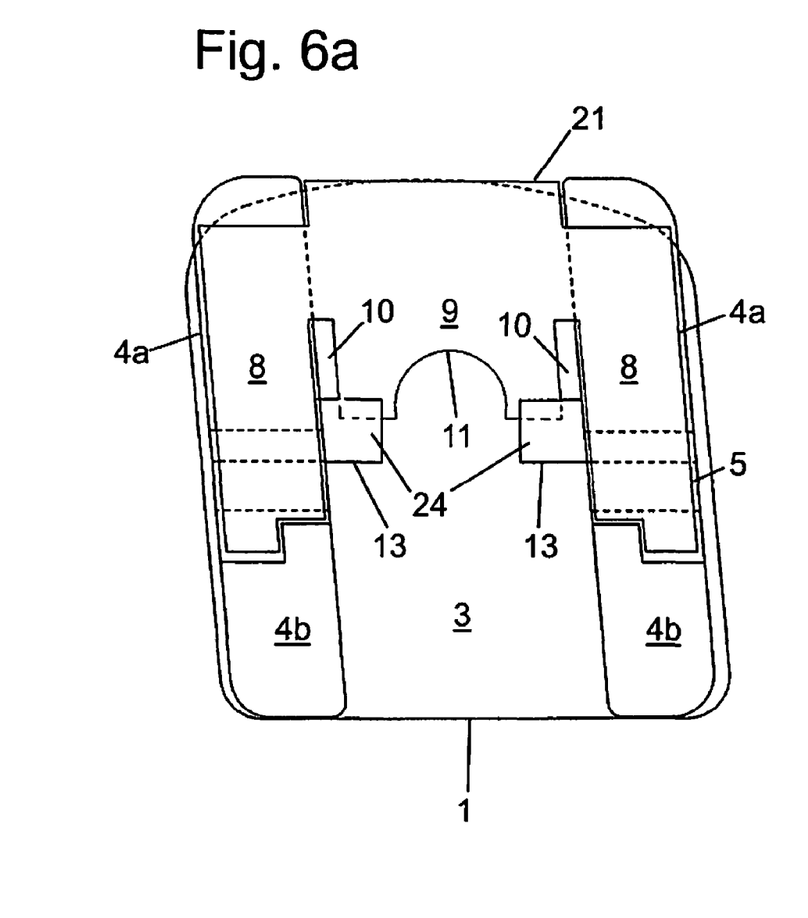
FIGS. 6a and 6b show top views of brackets according to the first embodiment of the invention for use on different teeth.
Figure 6B:
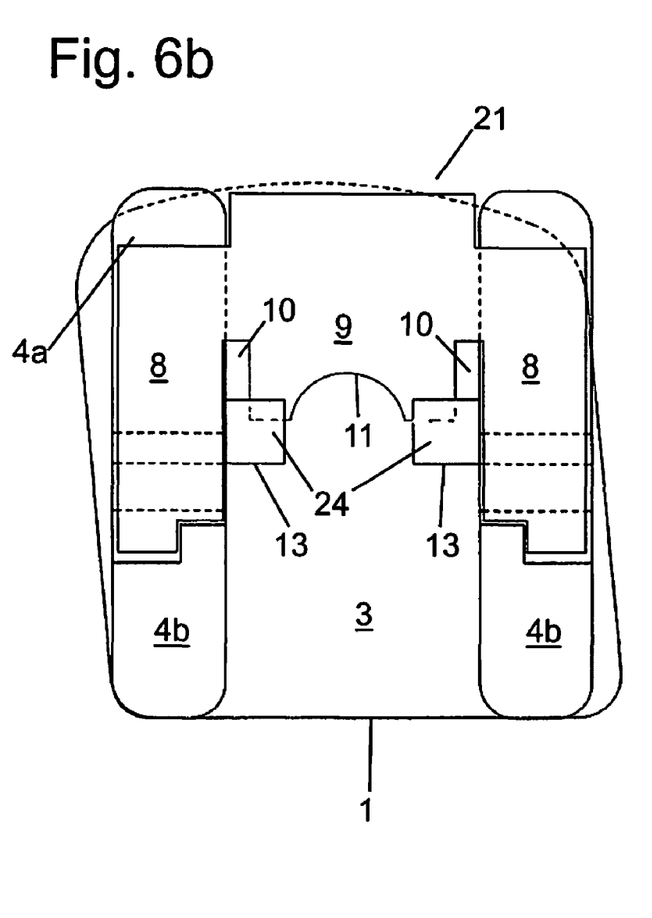

FIGS. 6a and 6b show top views of two embodiments of the inventive brackets for use on different teeth. The embodiment of FIG. 6a differs from that of FIG. 6b in that the upper bracket structure, and correspondingly also the closing spring, have the form of a parallelogram. The embodiment of FIG. 6b is configured generally as a rectangle. These figures are therefore intended to show that the invention can be applied to all bracket configurations, regardless of the location in the row of teeth to be corrected where the bracket is to be used.

Figure 7A:
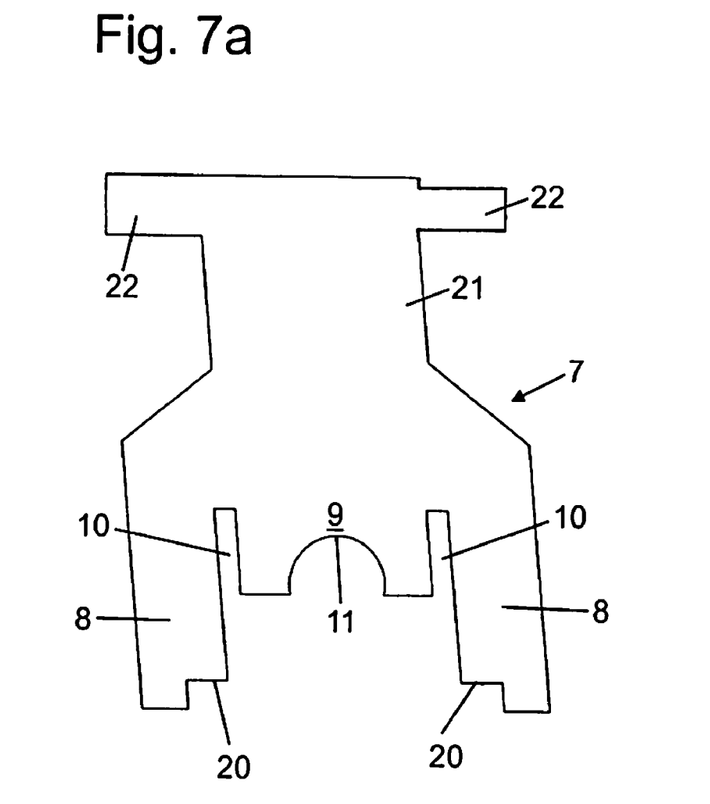
FIGS. 7a and 7b show developed views of the closing springs belonging to the brackets of FIGS. 6a and 6b.
Figure 7B:
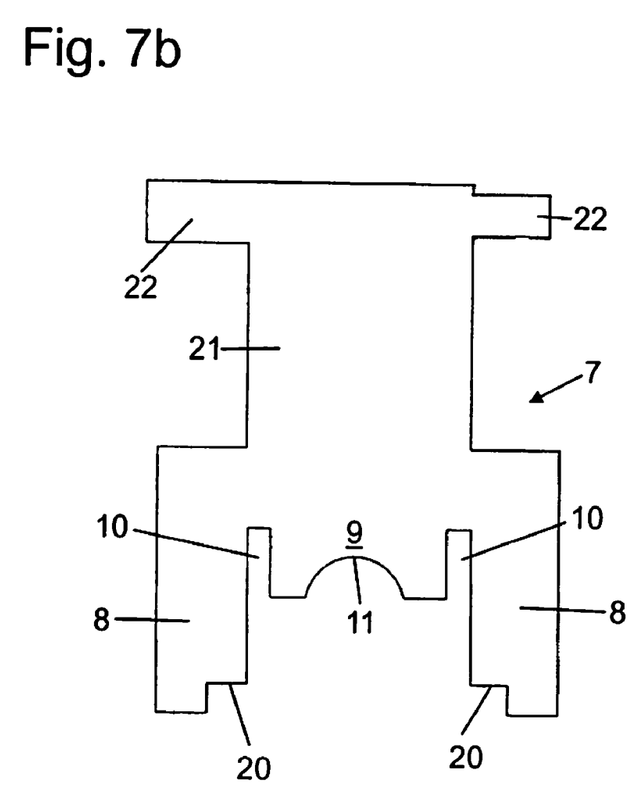

FIGS. 7a and 7b show developed views of the closing springs 7 belonging to the brackets of FIGS. 6a and 6b. It is possible to see clearly here the reduced-width section 21, which is intended to form the arc; the laterally projecting tabs 22, which are formed on the end of the arc and which are intended to form the pivot bearings; and the centering sections 20 on the free ends of the ligating tongues 8.

FIGS. 8a-8c and FIG. 9 show a second embodiment of the invention, in which one ligating tongue 8 is formed on the closing spring 7 between two latching tongues 9, the tongues being separated from each other by notches 10. Devices with an undercut 12 are provided on the second tie wing 4b of the upper bracket structure 4. Such devices hold the free ends 25 of the latching tongues 9 in the closed position of the closing spring 7. These devices are formed by a projection 13, which is formed on the second tie wing 4b and lies on the other side of the slot 5 provided in the upper bracket structure 4 to receive an arch wire 6. In the example shown here, the ligating tongue 8 is shorter than the latching tongues 9, so that the ligating tongue 8 is able to fit into the slot 5 when the closing spring 7 is closed. So that the ligating tongue can assume this position, at least the first tie wing 4a of the upper bracket structure 4 must comprise a gap extending transversely to the longitudinal direction of the slot 5. If this gap also extends into the second tie wing 4b, the ligating tongue 8 does not have to be shortened.

A bracket of this type can therefore be used as an active bracket, as already described above.

Figure 8A:
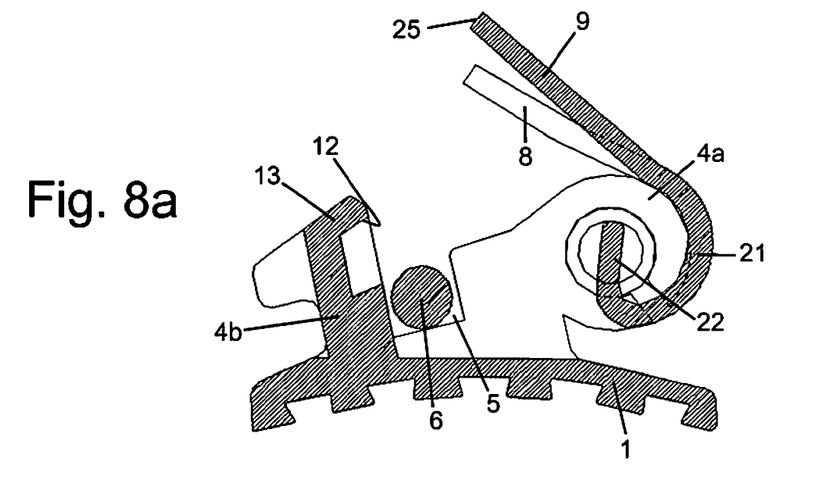
FIGS. 8a-8c show side views of a second embodiment of an inventive bracket similar to the views of FIGS. 5a-5c with the closing spring in different positions.
Figure 8B:
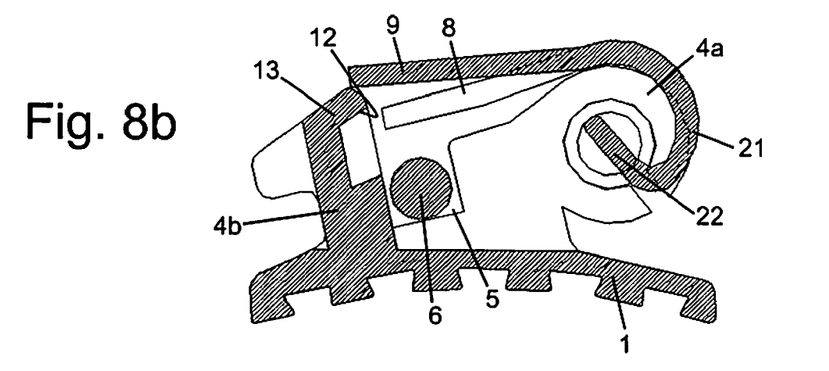
Figure 8C:
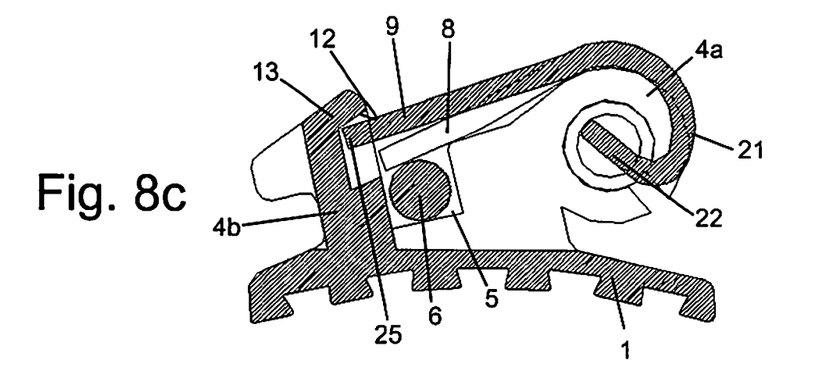

FIGS. 8a-8c show the second embodiment of the invention with the closing spring 7 in various states. FIG. 8a shows the completely opened position, in which the slot 5 has been completely opened for the insertion or removal of an arch wire 6. The arc 21 of the closing spring 7 adjacent to the first spring end 22 is under pre-tension, which tries to curve the arc inward. This pre-tension is able to clamp the closing spring 7 frictionally to the first tie wing 4a, so that the closing spring 7 is held in the opened state shown in FIG. 8a without the need for any further measures.

FIGS. 8a and 8b, show transition states during the closing of the closing spring 7. As can be seen, closing spring is curved in such a way during its fabrication that, in the resting state of the tongues 8 and 9 of the closing spring 7, the ligating tongue 9 projects farther than the latching tongues 8 toward slot 6. This has the result that, when the closing spring 7 is in the completely closed state shown in FIG. 8c, the ligating tongue 9 rests with pretension on the arch wire 6 lying in the slot 5 and thus presses it down onto the base of the slot. The free ends 25 of latching tongues 8 lie under the undercut 12 on projection 13 on second tie wing 4b and are supported thereon, thus holding the closing spring 7 in position against the force of reaction originating from the ligating tongue 9.

As will be understood, when the second tie wing 4b is divided by a gap, the two sections of the second tie wing 4b located at the sides of the gap are each provided with a projection 13 and an undercut 12. Such construction is best shown in the first embodiment illustrated in FIGS. 1 and 2, but is similar in the embodiment of FIGS. 8 and 9.

Figure 9:
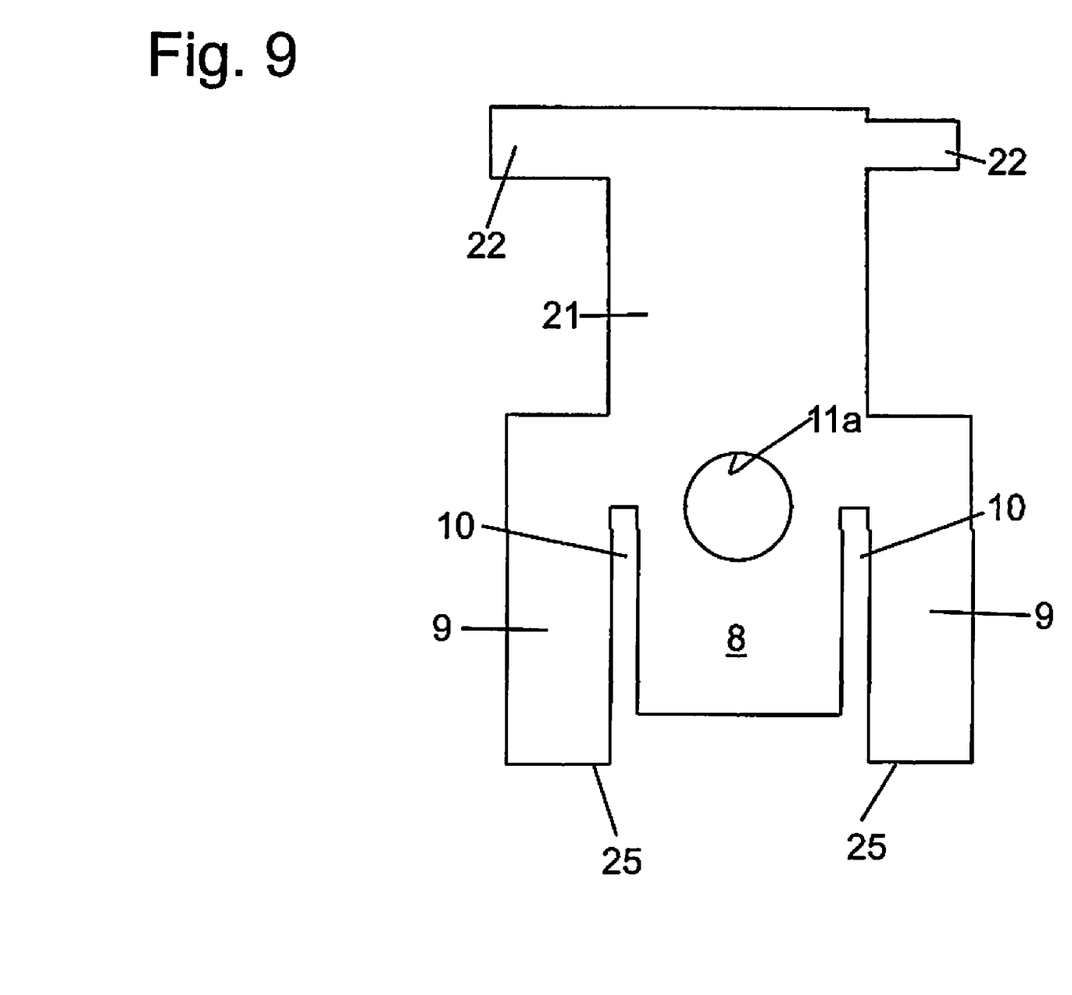
FIG. 9 shows the developed state of the closing spring belonging to the brackets of FIGS. 8a-8c.

FIG. 9 shows a developed view, from above, of the closing spring 7 of the embodiment according to FIGS. 8a-8c. It is possible to see the different lengths of the latching tongues 9 and the ligating tongue 8. A hole 11a can also be seen in the root area of the ligating tongue 8. This serves to accept a needle-like tool (not shown), which the orthodontist uses when he wants to open and close the closing spring 7.

The other features of this embodiment are the same as those which have already been described on the basis of the example according to FIGS. 1-7b, for which reason there is no need to explain these features again here.

It should also be noted that the second embodiment of the invention can also be modified in such a way that only one latching tongue is provided, which is framed laterally by two ligating tongues. In this case, the ligating tongues can be pushed up elastically, individually and to different degrees, by an arch wire lying in the slot when, for example, the arch wire is not resting flat over its entire length on the base of the groove but is rather elevated on one side in correspondence with the malposition of the tooth to be corrected. On the basis of the explanation of FIGS. 8a-9 above, those of ordinary skill in the art will fully understand how the upper bracket structure will have to be adapted to accommodate such operation and, as such, these modifications have not been specifically illustrated herein.

While the principles of the invention have been shown and described in connection with specific embodiments, it is to be understood that such embodiments are by way of example and are not limiting.

What is claimed is:

1. In a self-ligating orthodontic bracket including: (a) a base member having a base plate with a bottom side adapted to be attached to a tooth and a top side from which upper structure extends upwardly, the upper structure having first and second tie wings between which there is an arch-wire-receiving slot, at least one undercut being formed on the upper structure; and (b) a closing spring member having a first end which can be pivotably anchored to the first tie wing and a second end which is formed by three tongues, at least one of which is a latching tongue releasably engageable with the undercut and at least one other of which is a ligating tongue, the tongues being separated from each other by notches, the closing spring member being pivotable between an open position in which the slot is freely accessible for insertion of an arch wire and a closed position in which the at least one ligating tongue covers the arch wire in the slot and the at least one latching tongue is engaged with the undercut, the improvement wherein the closing spring member is detachably connected to the upper bracket structure, the tongues are substantially parallel, and in the closed position of the closing spring member the at least one ligating tongue is pre-tensioned toward the slot.

2. The orthodontic bracket of claim 1 including:
two ligating tongues and one latching tongue therebetween, the latching tongue having a free edge and being shorter than the ligating tongues such that the free edge of the latching tongue does not extend over the slot when the closing spring member is in the closed position;
and the upper structure has a projection forming the undercut positioned for engagement by the latching tongue when the closing spring member is in the closed position.

3. The orthodontic bracket of claim 2 comprising a pair of such undercut-forming projections alongside the slot, the undercuts of such projections each being engaged by the latching tongue when the closing spring member is in the closed position.

4. The orthodontic bracket of claim 3 wherein the free edge of the latching tongue forms a curved recess.

5. The orthodontic bracket of claim 3 wherein:
the upper bracket structure has a gap which is transverse to the slot and divides the first tie wing into two first-tie-wing portions and the second tie wing into two second-tie-wing portions;
each of the ligating tongues has a lateral cutout in its free end, the two cutouts being substantially symmetric to each other;
an upper edge of the slot in the each of the second-tie-wing portions forms the boundary of a contact surface thereon for a respective one of the ligating tongues; and
each of the second-tie-wing portions has an upward part projecting upwardly from its respective contact surface, the upward parts being configured and positioned for engagement with the ligating-tongue cutouts when the closing spring member is in the closed position, thereby to center the closing spring member.

6. The orthodontic bracket of claim 2 wherein the free edge of the latching tongue forms a curved recess.

7. The orthodontic bracket of claim 2 wherein:
the upper bracket structure has a gap which is transverse to the slot and divides the first tie wing into two first-tie-wing portions and the second tie wing into two second-tie-wing portions;
each of the ligating tongues has a lateral cutout in its free end, the two cutouts being substantially symmetric to each other;
an upper edge of the slot in the each of the second-tie-wing portions forms the boundary of a contact surface thereon for a respective one of the ligating tongues; and
each of the second-tie-wing portions has an upward part projecting upwardly from its respective contact surface, the upward parts being configured and positioned for engagement with the ligating-tongue cutouts when the closing spring member is in the closed position, thereby to center the closing spring member.

8. The orthodontic bracket of claim 1 wherein:
the upper bracket structure has a gap which is transverse to the slot and divides the first tie wing into two first-tie-wing portions and the second tie wing into two second-tie-wing portions with two latching tongues and one ligating tongue therebetween, the ligating tongue extends through the closing spring member; and
one of the undercuts is formed on each of the second-tie-wing portions in position for engagement with a respective one of the latching tongues of the closing spring member when it is in the closed position.

9. The orthodontic bracket of claim 1 wherein:
the first tie wing is divided into two first-tie-wing portions by a gap extending transversely to the slot;
a bore substantially parallel to the slot extends through each of the first-tie-wing portions, the bores being substantially coaxial; and
the first end of the closing spring member includes a pair of tabs extending in opposite directions, each tab being configured and positioned to be held in a respective one of the bores to facilitate pivoting of the closing spring member.

10. The orthodontic bracket of claim 9 wherein:
one of the first-tie-wing portions includes a feed opening which (a) extends to the bore, (b) is substantially radial with respect thereto, (c) faces the top side of the base plate, and (d) is positioned and arranged to facilitate mounting of the closing spring member onto the first-tie-wing portions; and a bearing bush is pressed into the bore having the feed opening to surround the tab in such bore.

11. The orthodontic bracket of claim 1 wherein the closing spring member has an arc portion pressed elastically against the first tie wing by its intrinsic pre-tension such that the pre-tension firmly clamps the closing spring frictionally against the first tie wing when the closing spring member is in the open position.

12. The orthodontic bracket of claim 1 wherein the closing spring member is of spring steel.

13. A base member for a self-ligating orthodontic bracket comprising:
   a base plate with a bottom side adapted to be attached to a tooth and a top side from which upper structure extends upwardly, the upper structure including first and second tie wings between which there is an arch-wire-receiving slot, the first tie wing being divided into two first-tie-wing portions by a gap transverse to the slot, each of the first-tie-wing portions having a bore therein substantially parallel to the slot extends, the bores being coaxial, and one of the first-tie-wing portions having a feed opening which (a) extends to the bore, (b) is substantially radial with respect to the bore, (c) faces the top side of the base plate, and (d) is open when the bracket is mounted on the base plate allowing assembly and disassembly of a closing member.

* * * * *